US008540719B2

(12) United States Patent
Peukert et al.

(10) Patent No.: US 8,540,719 B2
(45) Date of Patent: Sep. 24, 2013

(54) PERCUTANEOUS ROD INSERTION SYSTEM AND METHOD

(75) Inventors: Andrea Peukert, Tuttlingen (DE); Alexander Haas, Donaueschingen (DE); Matthew Kovach, Steamboat Springs, CO (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 320 days.

(21) Appl. No.: 12/702,560

(22) Filed: Feb. 9, 2010

(65) Prior Publication Data

US 2011/0196426 A1    Aug. 11, 2011

(51) Int. Cl.
*A61B 17/70* (2006.01)

(52) U.S. Cl.
USPC .......................... 606/86 A; 606/103; 606/99

(58) Field of Classification Search
USPC ....... 606/86 A, 103, 104, 914–916, 250–279, 606/99; 403/389, 391; 81/451–455
See application file for complete search history.

(56) References Cited

U.S. PATENT DOCUMENTS

| 5,129,388 | A | * | 7/1992 | Vignaud et al. ............... 606/258 |
| 5,954,635 | A | | 9/1999 | Foley et al. |
| 7,160,300 | B2 | | 1/2007 | Jackson et al. |
| 7,282,064 | B2 | | 10/2007 | Chin et al. |
| 7,318,825 | B2 | * | 1/2008 | Butler et al. ..................... 606/71 |
| 7,465,306 | B2 | | 12/2008 | Pond et al. |
| 7,476,240 | B2 | | 1/2009 | Raymond et al. |
| 7,491,208 | B2 | | 2/2009 | Pond et al. |
| 7,491,218 | B2 | | 2/2009 | Landry et al. |
| 7,520,879 | B2 | | 4/2009 | Justis et al. |
| 7,547,318 | B2 | | 6/2009 | Birkmeyer et al. |
| 7,572,276 | B2 | * | 8/2009 | Lim et al. ....................... 606/246 |
| 8,298,235 | B2 | * | 10/2012 | Grinberg et al. ............ 606/86 A |
| 8,328,853 | B2 | * | 12/2012 | Ibrahim et al. ................. 606/282 |
| 2004/0215190 | A1 | | 10/2004 | Nguyen et al. |
| 2005/0085813 | A1 | | 4/2005 | Spitler et al. |
| 2005/0131422 | A1 | | 6/2005 | Anderson |
| 2005/0245928 | A1 | * | 11/2005 | Colleran et al. ................ 606/61 |
| 2005/0277934 | A1 | * | 12/2005 | Vardiman ........................ 606/61 |
| 2006/0235398 | A1 | * | 10/2006 | Farris et al. ..................... 606/69 |
| 2006/0247630 | A1 | * | 11/2006 | Iott et al. ........................ 606/61 |
| 2006/0264934 | A1 | | 11/2006 | Fallin etal. |
| 2006/0264962 | A1 | | 11/2006 | Chin et al. |

(Continued)

FOREIGN PATENT DOCUMENTS

| DE | 10027988 | 1/2002 |
| EP | 1929967 | 6/2008 |

(Continued)

*Primary Examiner* — Jan Christopher Merene
(74) *Attorney, Agent, or Firm* — RatnerPrestia (57) ABSTRACT

Instruments and methods for inserting a spinal fixation rod include various components for inserting a rod with visual guidance. One kit includes a plurality of hollow elongated extension tubes and rod templates. The tube connectors connect the extension tubes in series. Another kit includes a rod guidance instrument having a sleeve. A guide member is attachable to the midsection of the sleeve, and a spinal fixation rod is attachable to the distal end of the sleeve. A method for inserting a spinal fixation rod into a plurality of rod receiving implants includes the steps of contouring a fixation rod to conform to a predetermined shape, contouring a guide member to match the shape of the contoured rod, and guiding the fixation rod into a rod receiving implant by maneuvering the guide member through a guide slot representing the location of the rod receiving implant.

24 Claims, 9 Drawing Sheets

(56) References Cited

U.S. PATENT DOCUMENTS

| | | |
|---|---|---|
| 2007/0173831 A1 | 7/2007 | Abdou |
| 2007/0233079 A1 | 10/2007 | Fallin et al. |
| 2008/0051781 A1 | 2/2008 | Geist et al. |
| 2008/0077136 A1 | 3/2008 | Triplett et al. |
| 2008/0077138 A1 | 3/2008 | Cohen et al. |
| 2008/0119850 A1 | 5/2008 | Sicvol et al. |
| 2008/0125788 A1 | 5/2008 | Cohen et al. |
| 2008/0161857 A1 | 7/2008 | Hestad et al. |
| 2008/0228228 A1 | 9/2008 | Hestad et al. |
| 2009/0036895 A1 | 2/2009 | Marino |
| 2009/0082809 A1 | 3/2009 | Nguyen et al. |
| 2009/0082811 A1 | 3/2009 | Stad et al. |
| 2009/0131755 A1 | 5/2009 | White et al. |
| 2009/0138044 A1 | 5/2009 | Bergeron et al. |
| 2009/0138056 A1 | 5/2009 | Anderson et al. |
| 2009/0143828 A1* | 6/2009 | Stad et al. .................. 606/86 A |
| 2009/0163924 A1 | 6/2009 | Justis et al. |
| 2011/0172714 A1* | 7/2011 | Boachie-Adjei et al. ..... 606/264 |

FOREIGN PATENT DOCUMENTS

| | | |
|---|---|---|
| WO | WO2007/021588 | 2/2007 |
| WO | WO2007/092870 | 8/2007 |
| WO | WO2007/146833 | 12/2007 |
| WO | WO2008/024937 | 2/2008 |
| WO | WO2009/055026 | 4/2009 |
| WO | WO2009-069025 | 6/2009 |

* cited by examiner

PERCUTANEOUS ROD INSERTION SYSTEM AND METHOD

FIELD OF THE INVENTION

The present invention relates generally to spinal fixation, and more specifically to components and methods for inserting a spinal fixation member with visual guidance.

BACKGROUND OF THE INVENTION

In many spinal fixation procedures, a spinal fixation rod is connected to implants attached to two or more vertebrae. When pedicle screws are used, the spinal fixation rod can be inserted into a rod receiving component associated with each pedicle screw. Minimally invasive procedures can make rod insertion difficult, because the surgeon only makes small incisions to insert each pedicle screw. Once the pedicle screws are attached to the vertebrae, the rod receiving components are not visible beneath the incisions. Inserting a spinal fixation rod through a first pedicle screw and navigating the rod beneath tissue into a second pedicle screw is very challenging. Minimally invasive procedures, such as percutaneous procedures, are disfavored in multi-level cases because of the difficulty in guiding the spinal fixation rod through small incisions and beneath tissue. This is particularly the case where the pedicle screws have different heights and/or medial lateral positions, forming a non-linear path to which the rod must conform.

In cases where the pedicle screws are not aligned, some surgeons choose a manual insertion approach in which the surgeon guides the rod and uses tactile feedback, with or without x-ray imaging, to check the position of the rod relative to the implants. This process is extremely difficult, and does not provide the surgeon with any way to accurately determine the proper length and curvature for the rod. Other surgeons use extensions connected to the implants to assist in inserting the rod. These mechanical approaches typically do not work in multi-level cases where the heights of the implants and/or medial-lateral positions of the implants are substantially offset from one another.

SUMMARY OF THE INVENTION

In a first aspect of the invention, a kit for guiding the insertion of a spinal fixation rod includes a plurality of hollow elongated extension tubes. Each extension tube has an implant engaging end and a template end. The kit also includes a plurality of tube connectors that connect the extension tubes in series. Moreover, the kit includes a plurality of rod templates, each rod template comprising a rod receiving channel.

In a second aspect of the invention, a kit for guiding the insertion of a spinal fixation rod includes a rod guidance instrument. The rod guidance instrument has a sleeve with a proximal end, a distal end and a midsection between the proximal end and distal end. An elongated guide member is attachable to the midsection of the sleeve, and a spinal fixation rod is attachable to the distal end of the sleeve.

In a third aspect of the invention, a method for inserting a spinal fixation rod into a plurality of rod receiving implants includes the steps of contouring a spinal fixation rod to conform to a predetermined shape, contouring an elongated guide member to match to the predetermined shape of the spinal fixation rod, interconnecting the spinal fixation rod and elongated guide member, inserting the spinal fixation rod through an incision while maintaining the guide member above the incision, guiding the spinal fixation rod into a first rod receiving implant by maneuvering the guide member through a guide slot representing the location of the first rod receiving implant, and guiding the spinal fixation rod into a second rod receiving implant by maneuvering the guide member through a guide slot representing the location of the second rod receiving implant.

BRIEF DESCRIPTION OF THE DRAWINGS

The foregoing summary and the following detailed description will be better understood in conjunction with the drawing figures, of which.

DETAILED DESCRIPTION OF EMBODIMENTS OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Rod insertion systems in accordance with the invention utilize visual guides that simulate the movement and relative position of a spinal fixation rod during a rod insertion procedure. While the systems can be used in various rod insertion procedures, the systems are particularly useful for percutaneous procedures and other rod insertion approaches where small incisions are made, and where the rod is being placed over two or more levels. In such cases, the implanted pedicle screws are not typically arranged in a straight line configuration. Rather, the rod receiving channels of the implants are typically offset from one another, forming a complex serpentine or other non-linear path to which the rod must conform. The patient's tissue presents a visual obstruction that prevents the surgeon from seeing the shape of the path, making it very difficult or impossible for the surgeon to determine the required rod length and curvature without using imaging technology. During rod insertion, the obstructing tissue prevents the surgeon from seeing where a fixation rod is located in relation to each implant and the overall path. The visual guides provided by exemplary embodiments of the invention allow the surgeon to visualize and precisely determine the required rod length and curvature. Once the rod length and curvature are set, the visual guides allow the surgeon to navigate the rod through multiple implants with precision while the rod is obstructed from view beneath tissue.

As will be explained below, exemplary systems in accordance with the invention may include extension tubes than can be pre-assembled to pedicle screws before the screws are implanted. This avoids difficulties that can be experienced when attempting to connect an extension tube to an implanted pedicle screw that is concealed beneath tissue.

Exemplary systems in accordance with the invention may also include templates that can be connected to or integrally formed with the extension tubes. The templates extend above the tissue, where they allow the surgeon to easily assess the required length and curvature of a fixation rod to be inserted. In particular, the templates illustrate the precise path through which the fixation rod must be navigated, allowing the surgeon to select a rod of proper length and adjust the curvature of the selected rod as needed, prior to inserting the rod.

Exemplary systems in accordance with the invention may further include tube connectors to secure the extension tubes in a fixed relationship in which the tubes are maintained parallel to one another. In this relationship, the proximal ends of the tubes represent the relative positions of the corresponding implant because the extension tubes have the same length. The proximal ends of the parallel tubes can incorporate templates, which represent the rod receiving channels of each corresponding implant from which the tube extends. In one embodiment, the tube connectors are in the form of rings that slide over the extension tubes, and the templates are in the form of U-shaped notches at the proximal ends of the extension tubes.

Exemplary systems in accordance with the invention may further include a rod insertion instrument with a guide member that provides the surgeon with a visual aid during insertion of the rod. In one embodiment, a double-rod insertion instrument features a mount for a fixation rod and a separate mount for a guide member or "dummy rod". During insertion of the fixation rod, the guide member mimics the movement of the fixation rod, providing a visual guide that allows the surgeon to navigate the fixation rod without actually seeing the fixation rod.

By way of a first example, the present invention may be embodied in a surgical kit. The kit may include:

a plurality of hollow elongated extension tubes, each extension tube having an implant engaging end, a template end, and an engagement surface on the outside of the extension tube, the engagement surface having a contour;

a plurality of tube connectors joinable in series, each tube connector comprising a ring surrounding a central opening, the central opening bounded by an inner wall inside the ring, the inner wall having a contour that conforms to the contour of the engagement surface of one of the extension tubes, each tube connector further comprising one or more couplings joinable to another of the plurality of tube connectors; and a plurality of rod templates, each rod template comprising a rod receiving channel.

By way of a second example, the present invention may be embodied in a surgical kit that includes:

a rod guidance instrument comprising:

a sleeve having a handle end and a rod engagement end opposite the handle end, the sleeve comprising a midsection between the handle end and the spinal rod engagement end; and an elongated guide member attached to the midsection of the sleeve;

and a spinal fixation rod attached to the rod engagement end of the sleeve.

By way of a third example, the present invention may be embodied in a method for inserting a spinal fixation rod into a plurality of rod receiving implants, the method comprising the steps of:

contouring a spinal fixation rod to conform to a predetermined shape;

contouring an guide member to match to the predetermined shape of the spinal fixation rod;

interconnecting the spinal fixation rod with the guide member so that the spinal fixation rod and guide member are moveable in unison with one another;

inserting the spinal fixation rod through an incision while maintaining the guide member above the incision;

guiding the spinal fixation rod into a first rod receiving implant by maneuvering the guide member through a guide slot representing the location of the first rod receiving implant; and guiding the spinal fixation rod into a second rod receiving implant by maneuvering the guide member through a guide slot representing the location of the second rod receiving implant.

In any of the foregoing examples, a visual guide member in the form of a dummy rod may be used to replicate the movement of the spinal fixation rod during insertion of the spinal fixation rod. The guide member and spinal rod are coupled to one another on an insertion instrument so as to move in unison. Markers are present above the incisions to represent the position of each rod receiver relative to the spinal fixation rod. The surgeon maneuvers the guide member through each marker. As this is done, the spinal rod moves in unison with, but offset from, the guide member to navigate through each rod receiver component beneath the incisions. Using this navigation system and procedure, the surgeon can guide the spinal fixation rod through multiple pedicle screws by observing the movement of the guide member through each marker.

Figure 1:
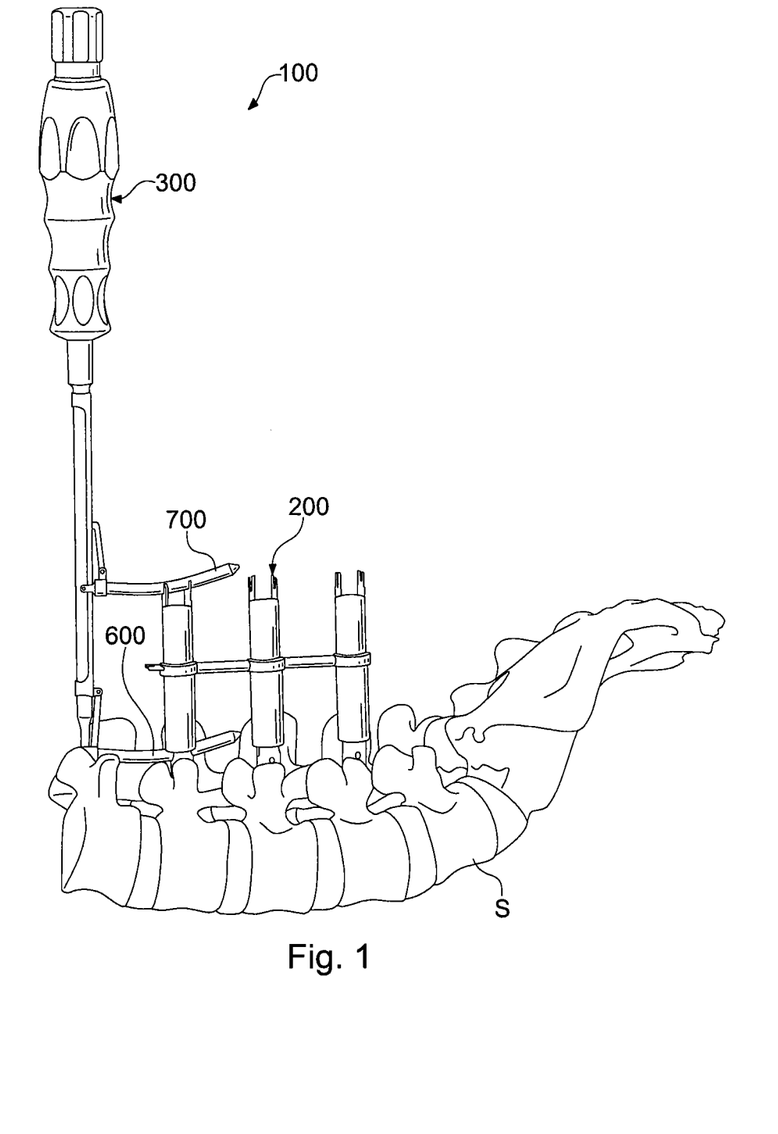
FIG. 1 is a perspective view of a kit for guiding the insertion of a spinal fixation rod in accordance with an exemplary embodiment of the invention, with components of the kit shown as they would be positioned relative to a section of the human spine.

Referring now to FIG. 1, a kit 100 in accordance with an example of the invention is shown with a model of a human spine "S". The model of the spine S is included to illustrate how kit 100 may be positioned relative to an actual spine, and does not form part of the invention. Kit 100 generally includes a rod guidance assembly 200 and a rod guidance instrument 300. Rod guidance assembly 200 and rod guidance instrument 300 are each designed specifically for the purpose of working with the other to guide the insertion of a spinal fixation member into multiple rod receiving components. Kit 100 includes a spinal fixation member in the form of a fixation rod 150.

Figure 2:
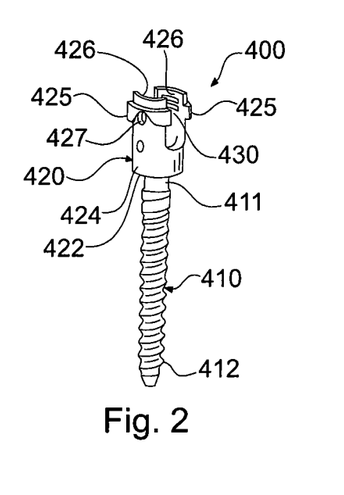
FIG. 2 is a perspective view of a pedicle screw in accordance with an exemplary embodiment of the invention.

Referring now to FIG. 2, a pedicle screw assembly 400 is shown in accordance with one exemplary embodiment of the invention. Assembly 400 includes a polyaxial bone screw 410 and a rod receiver 420. Bone screw 410 has a head 411 and a threaded shank 412. Rod receiver 420 has a hollow passage 430 for receiving bone screw 410. An opening 422 in rod receiver 420 allows shank 412 to pass through a base portion 424 of the rod receiver. Rod receiver 420 is generally cylindrical, but interrupted at two sections, forming diametrically opposed U-shaped channels 426. Channels 426 collectively form a transverse conduit through rod receiver 420 to receive a section of a spinal fixation rod.

Figure 3:
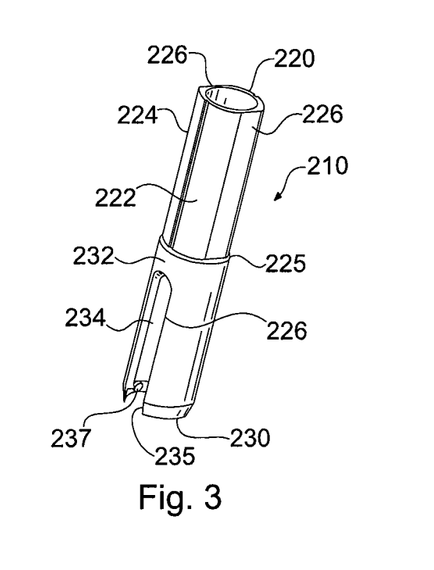
FIG. 3 is a perspective view of an extension tube in accordance with an exemplary embodiment of the invention.

Referring now to FIG. 3, rod guidance assembly 200 includes a plurality extension tubes. The extension tubes are identical or essentially identical in configuration. For simplicity, one extension tube 210 is shown and described, with the understanding that multiple extension tubes in the kit can have the same features and characteristics. Extension tube 210 is configured for attachment to a rod receiver, and may be attached to a rod receiver of a pedicle screw before the pedicle screw is implanted. Normally, the rod receiver portion of a pedicle screw does not project above an incision. The extension tube 210 provides a conduit to the pedicle screw that extends above the incision. Extension tube 210 is generally cylindrical and includes a proximal end 220, a proximal section 222, a distal end 230 and a distal section 232. Distal section 232 has a slightly larger outer dimension than proximal section 222, forming a sharp transition or stop 225 between the proximal and distal sections. Distal section 232 is interrupted at two sections, forming diametrically opposed U-shaped openings 226. Distal section 232 has an inner wall 234 that forms a socket 235 in the distal section.

Figure 4:
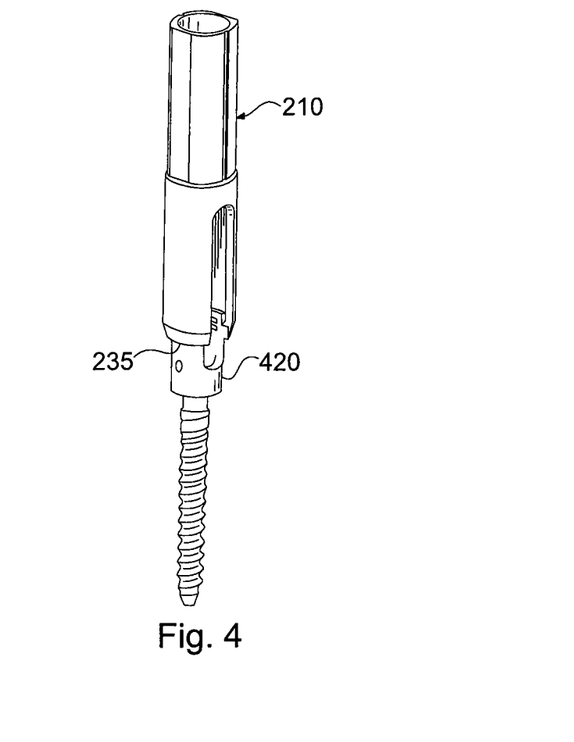
FIG. 4 is a perspective view of the pedicle screw of FIG. 2 and extension tube of FIG. 3 in an assembled condition.

Socket 235 is adapted to receive a rod receiver 420, as shown in FIG. 4. Inner wall 234 has a pair of diametrically opposed projections 237 that cooperatively engage a pair of diametrically opposed indentations 427 on the exterior of rod receiver 420. Projections 237 cooperatively engage indentations 427 to secure extension tube 210 over rod receiver 420. Rod receiver 420 further includes a pair of flanges 425 that allow extension tube 210 to be rotated into a locked engagement with the rod receiver, or rotated out of a locked engagement. Rod receivers in accordance with the invention may take one of several forms in addition to that shown, including but not limited to the configurations described in U.S. application Ser. No. 12/241,897, filed on behalf of the same Assignee, the contents of which are incorporated by reference herein in their entirety and for all purposes.

Figure 5:
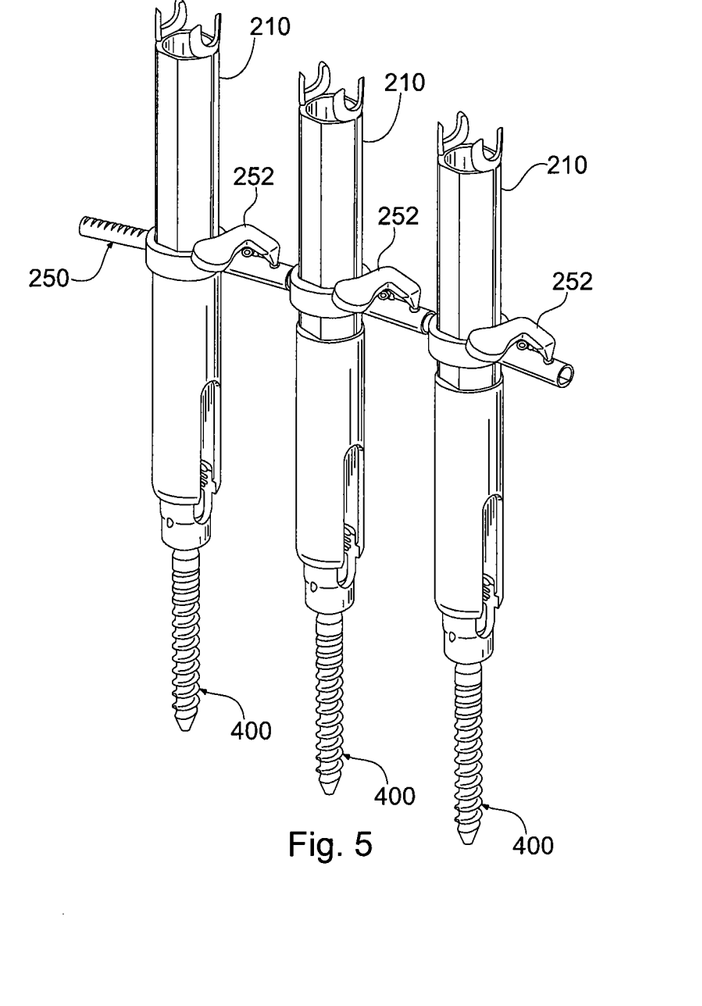
FIG. 5 is a perspective view of a series of pedicle screws and extension tubes joined by a connector mechanism in accordance with an exemplary embodiment of the invention.

Referring now to FIG. 5, components of a rod guidance assembly include three pedicle screw assemblies 400 and a tube connector assembly 250 that interconnects the pedicle screw assemblies. Tube connector assembly 250 attaches to extension tubes 210 associated with each pedicle screw assembly 400, as shown. Tube connector assembly 250 is configured to interconnect multiple extension tubes and maintain the extension tubes parallel to one another. In a parallel arrangement, the distance between distal ends of adjacent extension tubes is equal to the distance between the proximal ends. The distal ends of extension tubes are placed directly over rod receivers of pedicle screws. Therefore, the proximal ends of the extension tubes can be used to approximate the relative position of each rod receiver in three-dimensional space, which, as noted above, is typically not visible in the incision.

Once extension tubes are interconnected in a parallel arrangement, the proximal ends of the extension tubes can be used as a template to measure the required length of a spinal fixation rod to be inserted into the rod receiver components. In addition, the proximal ends can be used to accurately adjust the length and curvature of a spinal fixation rod to be placed in the rod receiver components. In many cases, the pedicle screws are not arranged in a linear arrangement, but are offset from one another relative to multiple planes of reference. Tube connector assembly 250 includes adjustable components, as described in more detail below, that adapt to these non-linear arrangements.

Referring now to FIGS. 6-10, tube connector assembly 250 includes a plurality of tube connectors that connect with one another to hold adjacent extension tubes in a parallel arrangement. The tube connectors include a first end component 260, a second end component 270 and one or more intermediate components 280. First end component 260, second end component 270 and intermediate component 280 each include connector rings 262, 272 and 282, respectively, for attachment around extension tubes. Connector rings 262, 272 and 282 have central openings 290 that are identically configured. Each opening 290 has an inner wall 292 that preferably conforms to the outer geometry of extension tubes 210. Extension tubes 210 preferably have identical outer geometries so as to mate with any of connector rings 262, 272 and 282. Proximal section 222 of each extension tube 210 has a generally cylindrical geometry and exterior surface 224. Exterior surface 224 has two diametrically opposed flat sections 226. Similarly, each opening 290 associated with a connector ring has an inner wall 292 having two diametrically opposed flat sections 296. Exterior surfaces 224 have dimensions that are identical or substantially identical to the dimensions of inner walls 292. In this arrangement, the connector rings are adapted to slide over the exterior of the proximal sections 222 of extension tubes 210. Openings 290 are adapted to receive proximal sections 222 of extension tubes 210 only when flat sections 226, 296 are axially aligned. As noted above, each extension tube 210 has a sharp transition or stop 225. Stops 225 limit the extent to which the connector rings 262, 272, 282 can be advanced over the tubes.

Figure 6:
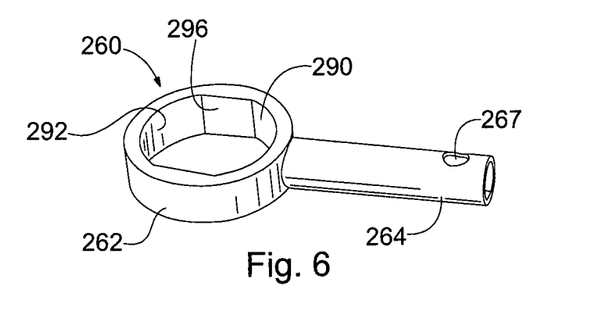
FIG. 6 is a perspective view of a first connector component in accordance with an exemplary embodiment of the invention.
Figure 7:
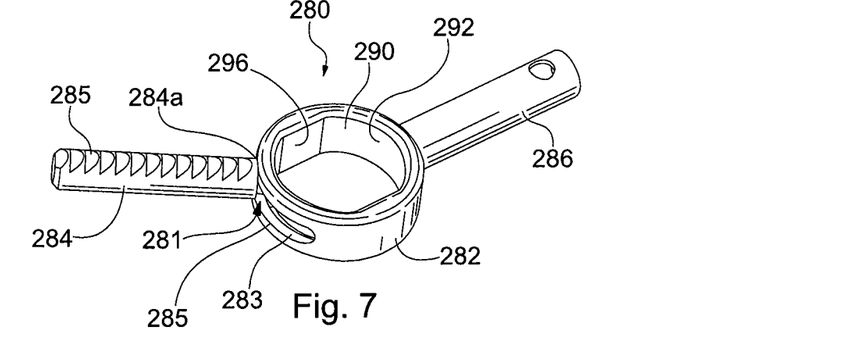
FIG. 7 is a perspective view of a second connector component in accordance with an exemplary embodiment of the invention.
Figure 8:
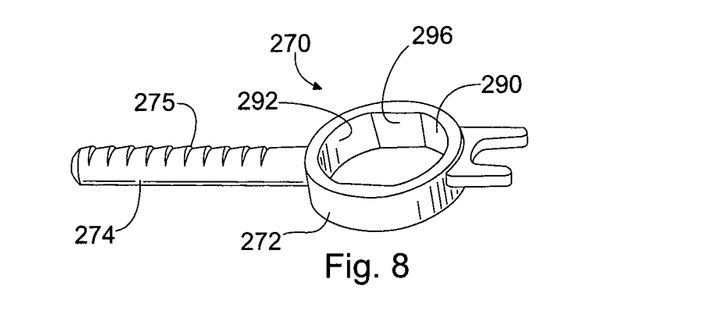
FIG. 8 is a perspective view of a third connector component in accordance with an exemplary embodiment of the invention.

The tube connector rings are preferably interconnected by a connection mechanism that adjusts to the spacing between extension tubes and adjusts to the alignment of extension tubes. Components 260, 270 and 280, for example, utilize telescoping connectors and angular adjustment mechanisms. More specifically, first end component 260 includes a tubular connector sleeve 264, and intermediate component 280 also includes a connector arm 284 that can be inserted into connector sleeve 264 to interconnect the first end component and intermediate component. Intermediate component 280 also includes a connector sleeve 286, and second end component 270 includes a connector arm 274 that can be inserted into connector sleeve 286 to interconnect the intermediate component and second end component.

Intermediate component 280 includes a pivot mechanism 281 that allows connector arm 284 to be pivotally displaceable. Pivot mechanism 281 is formed by an elongated window 283 extending along a section of the circumference of intermediate component 280. Window 283 forms a sliding track 285 within the wall of intermediate component 280. Connector arm 284 has a narrowed section 284a near one end of the arm, and a flange 284b adjacent the narrow section at the end of the arm. Narrowed section 284a has cross-sectional dimensions equal to or slightly less than the width of track 283. Flange 284b and the rest of connector arm 284 have cross-sectional dimensions greater than the width of the track. In this arrangement, connector arm 284 can be inserted through window at the narrowed section so that the connector arm is captive in window 283 at the narrow section. Flange 284b prevents connector arm 284 from being detached from the ring portion of intermediate component 280.

Flange 284b is slideable along track 283 and within window 281, forming a turret-type mechanism to adjust the orientation of connector arm 284 relative to the intermediate component 280. When components 260, 270 and 280 are interconnected, for example, connector arm 284 is pivotable with respect to the ring portion of intermediate component to adjust the relative orientations or alignment of components 260, 270 and 280 so that they align with the positions and orientations of extension tubes 210.

Figure 9:
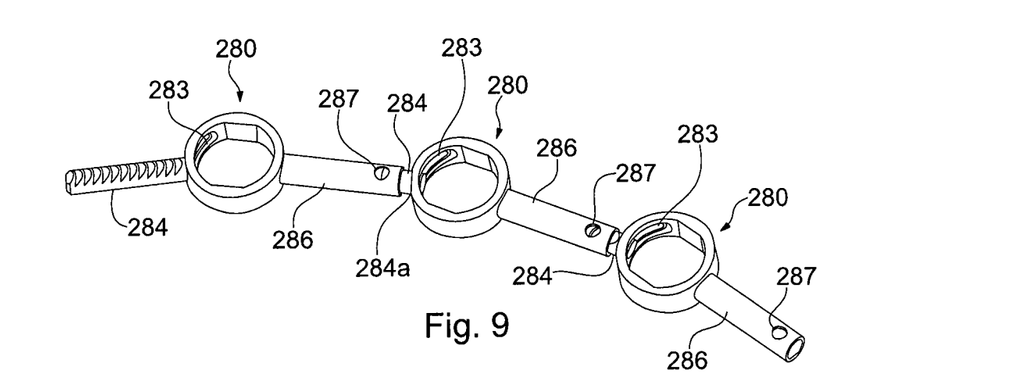
FIG. 9 is a perspective view of three connector components in accordance with the second connector component of FIG. 7, connected in series.

Tube connector assemblies that join three or more pedicle screws may have two or more pivot mechanisms, depending on the arrangement of pedicle screws. In such cases, two or more intermediate components 280 with pivot mechanisms 281 may be connected together in series. FIG. 9 illustrates three intermediate components 280 interconnected in series.

Figure 10:
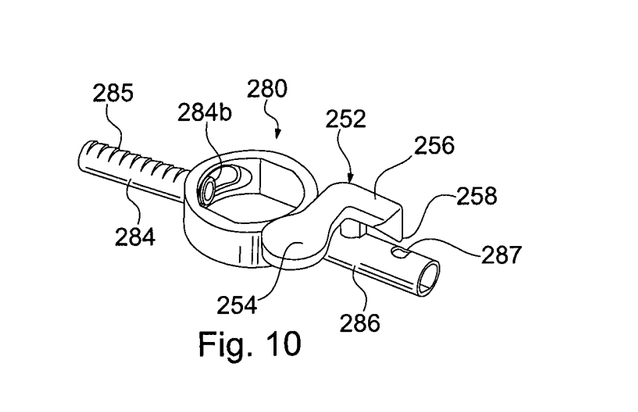
FIG. 10 is a perspective view of the second connector component of FIG. 7, shown with a locking component in accordance with an exemplary embodiment of the invention.

Connector arms 274, 284 can be inserted and advanced into connector sleeves 286, 264, respectively, to different depths to adjust the relative spacing between adjacent connector rings. Tube connector assembly 250 preferably includes mechanisms to maintain the insertion depth of connector arms and sleeves, thereby fixing the relative spacing between connector rings once the spacings are set. FIG. 10, for example, shows a latch 252 connected to connector sleeve 286 of intermediate component 280. Latch 252 has an L-shaped configuration, with a thumb pad 254 on one leg and a latch arm 256 forming the other leg. A pawl 258 extends from latch arm 256 toward connector sleeve 286. Pawl 258 aligns with an aperture 287 in connector sleeve 286. A similar aperture 267 is provided in connector sleeve 266 of first end component 260. Latch 252 is pivotally mounted to the exterior of connector sleeve 286, and is pivotable between a release position, in which pawl 258 is raised away from aperture as shown in FIG. 10, and a latching position, in which the pawl is lowered toward connector sleeve 286 into aperture 287. Multiple latches 252 can be used with a tube connector assembly, as shown in FIG. 5.

The crest or top portions of connector arms 274, 284 each have a series of slits 275, 285, respectively. Slits 275 and 285 are positioned on the connector arms to face the top interior portions of the connector sleeves 266 and 286, respectively. With this relative positioning, slits 275 are visible through aperture 287 when the connector arm 274 of second end member 270 is inserted into connector sleeve 286 of intermediate member 280. Similarly, slits 285 are visible through aperture 267 when the connector arm 284 of intermediate member 280 is inserted into connector sleeve 264 of first end member 260. Slits 275 and 285 are adapted to be engaged by a latch 252 to releasably lock the relative spacing between two connector rings. More specifically, slits 275 and 285 are individually adapted to receive pawl 258 of latch 252 when the slits are exposed through one of the apertures of the connector sleeves.

Rod guidance assembly 200 further includes one or more means for visually navigating and guiding a rod into rod receiving implants. In preferred embodiments, visual guidance means are provided at the proximal ends of the extension tubes. The guidance means may take the form of channel markers that represent the actual channels through which the fixation rod is being inserted. Channel markers in accordance with the invention may have the same shapes and dimensions as the rod receiving channels through the implants. When the same shapes and dimensions are used, a fixation rod can be navigated through the rod receiving channels on the implants with a very high level of precision.

Figure 11:
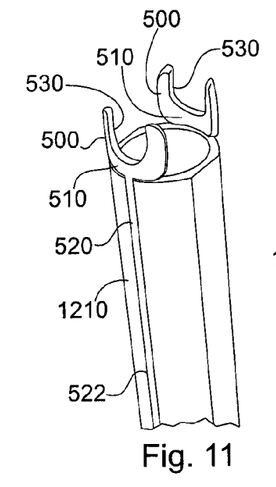
FIG. 11 is a truncated perspective view of a first extension tube with an insertion guide in accordance with an exemplary embodiment of the invention.
Figure 12:
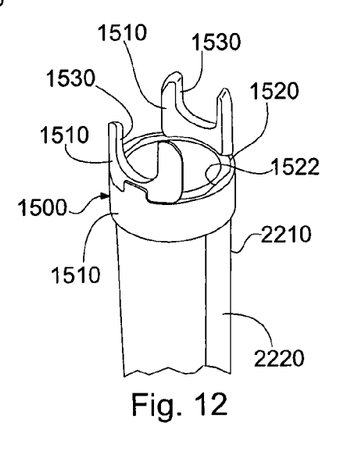
FIG. 12 is a truncated perspective view of a second extension tube with an insertion guide in accordance with an exemplary embodiment of the invention.
Figure 13:
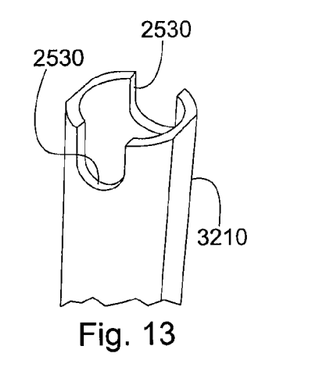
FIG. 13 is a truncated perspective view of a third extension tube with an insertion guide in accordance with an exemplary embodiment of the invention.

Referring to FIGS. 11-13, three examples of channel markers are shown in accordance with the invention. FIG. 11 shows an extension tube 1210 with a pair of removable channel markers 500. Each channel marker 500 includes a body portion 510 and a stem portion 520. Only one stem portion 520 is visible in FIG. 11. Body portion 510 forms a U-shaped channel 530. Extension tube 1210 has two diametrically opposed slots 522 that run longitudinally along the length of the extension tube. Only one slot 522 is visible in FIG. 11. The stem portion 520 of each marker 500 is sized for insertion into one of the slots 522 to detachably connect the marker to the extension tube. The U-shaped channels 530 have identical shapes and dimensions as the rod receiving channels on the implants.

FIG. 12 shows an alternate channel marker arrangement featuring a ring attachment 1500 placed over the proximal end of an extension tube 2210. Ring attachment 1500 includes a body portion 1510 that surrounds an opening 1520. Opening 1520 has a cross-sectional shape that conforms to the outer geometry of the proximal end of extension tube 2210. As with other embodiments, the outer geometry of extension tube 2210 has flat sections 2220 that engage flat sections 1522 inside opening 1520. Flat sections 1522 and 2220 prevent ring attachment 1500 from rotating about the proximal end of extension tube 2210. Ring attachment 1500 includes a pair of body portions 1510, each having U-shaped channels 1530. U-shaped channels 1530 have identical shapes and dimensions as the rod receiving channels on the implants. Flat sections 2220 of extension tube 2210 are offset from the rod receiving channels of the implant by 90 degrees. Likewise, flat sections 1522 on ring attachment 1500 are offset from U-shaped channels 1530 by 90 degrees. In this arrangement, flat sections 1522 and 2220 ensure that U-shaped channels 1530 are axially aligned with the rod receiving channels of the implant when ring attachment 1500 is placed over the extension tube. This alignment allows the U-shaped channels 1530 on an extension tube to represent the locations of the rod receiving channels of the implant connected to that extension tube.

FIG. 13 shows another channel marker arrangement where U-shaped channels 2530 are formed in the proximal end of an extension tube 3210 itself, as opposed to an attachment that connects to the extension tube. U-shaped channels 2530 have identical shapes and dimensions as the rod receiving channels on the implants.

Figure 14:
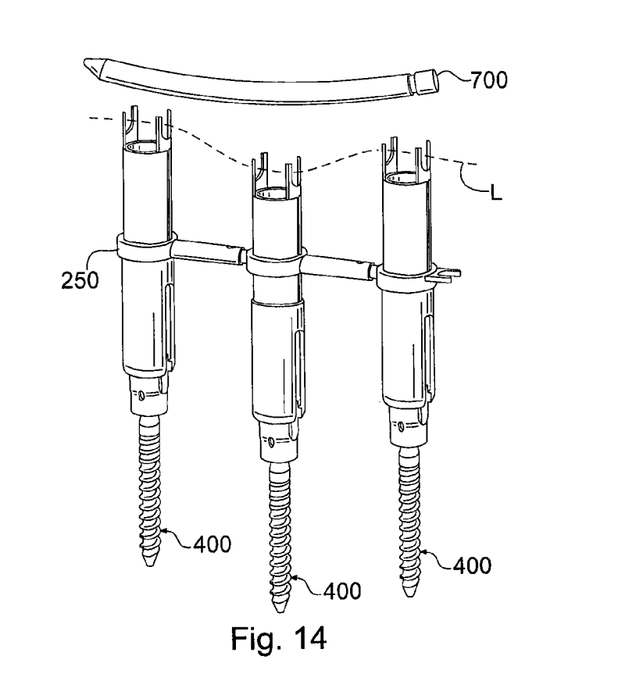
FIG. 14 is a perspective view of a series of pedicle screws with extension tubes and other components in accordance with an exemplary embodiment of the invention, the pedicle screws shown with a contoured guide member also in accordance with an exemplary embodiment of the invention.

Channel markers provide visual representations of the rod receiving channels on spinal implants. When channel markers are used together on a series of extension tubes, the channel markers provide a visual outline of how the rod needs to be shaped in order to pass through each implant. In many cases, the spinal implants and their rod receiving components are not arranged in a straight line, but instead follow a curved path, such as the curved path shown by the dashed line "L" in FIG. 14. Because the channel markers indicate the relative positions of the rod receiving channels on the spinal implants, the channel markers form a template that can be used to shape a fixation rod prior to insertion. The fixation rod may be bent and shaped to follow a curved path defined by channel markers. During the shaping process, the rod can be set periodically into the channel markers to monitor the shaping and confirm a proper shaping.

Referring now to FIGS. 15-18, rod guidance instrument 300 is shown in accordance with one exemplary instrument of the invention. Rod guidance instrument 300 is operable to insert a fixation rod into rod receiving implants that are beneath tissue and not visible to the surgeon. Instrument 300 is adapted to insert a fixation rod under virtual guidance that allows the rod to be navigated through the rod receiving channels of implants. Instrument 300 generally includes means for holding a fixation rod 600 at the distal end of the instrument, and means for holding a guide member 700 at a midportion of the instrument, as shown in FIG. 1.

Figure 15:
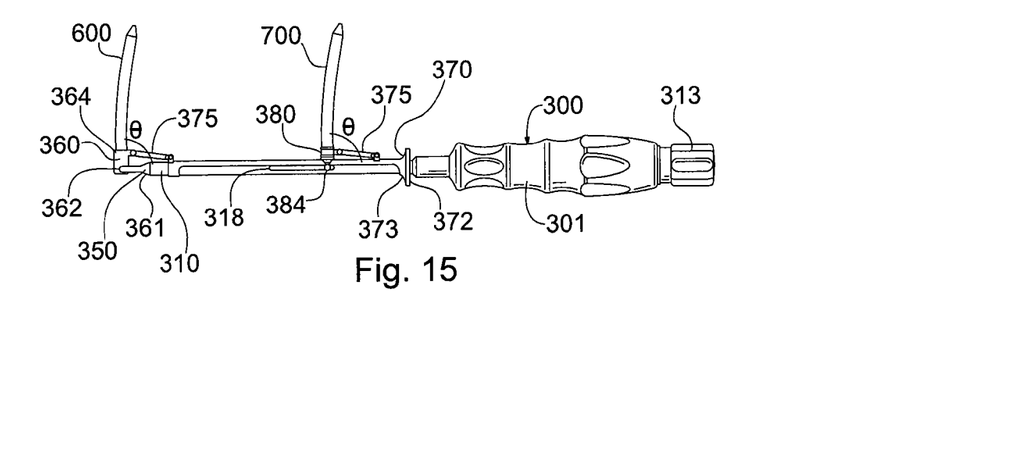
FIG. 15 is a side view of a rod insertion instrument, spinal fixation rod and guide member in accordance with exemplary embodiments of the invention, the instrument shown with the rod in a first position.
Figure 16:
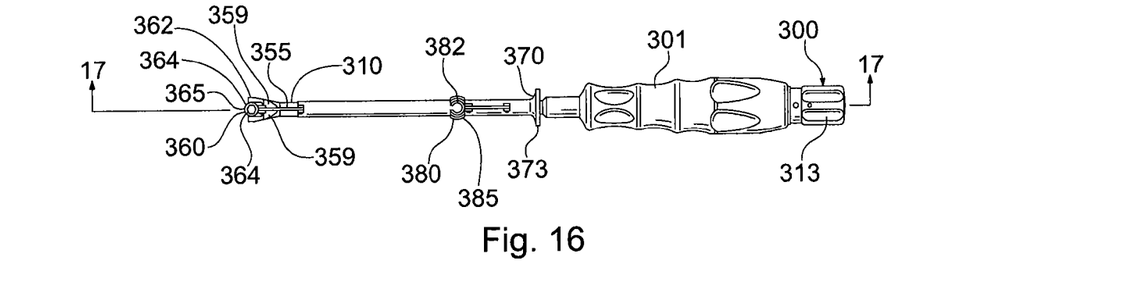
FIG. 16 is a front view of the rod insertion instrument of FIG. 15.
Figure 17:
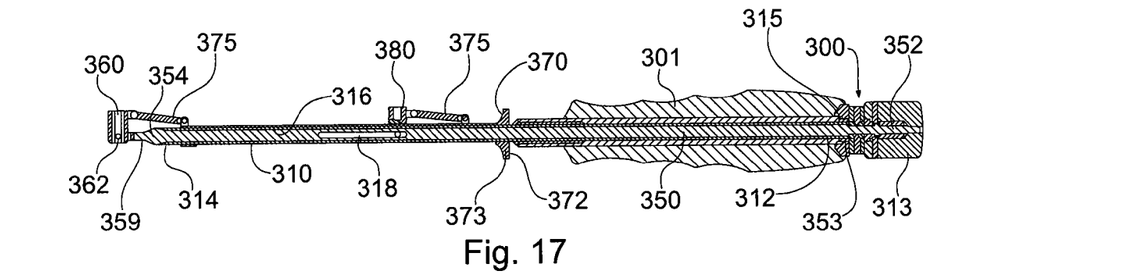
FIG. 17 is a side cross-section view of the rod insertion instrument of FIG. 15.

Rod guidance instrument 300 includes an outer sleeve 310 having a proximal end 312 and a distal end 314. A hollow knob portion 313 is attached to proximal end 312. Outer sleeve 310 is hollow and forms a central bore 316 that extends from proximal portion distal end 314. Knob portion 313 contains an internal thread 315. An inner shaft 350 extends through knob portion 313 and into bore 316 of outer sleeve 310. Inner shaft 350 has a proximal end 352 that extends inside knob portion 313, and a distal end 354 with a pair of jaws 359. A rod clamp 360 is pivotally attached to jaws 359 by a pin connection 362. Rod clamp 360 includes a pair of semi-cylindrical sections 364 that are coupled with one another to form a cylindrical socket 365. Jaws 359 are separated by a narrow slit 355. Each of the jaws 359 has a tapered section 361 that tapers outwardly toward the distal end of instrument 300. Tapered section 361 has a width larger than the diameter of bore 316 at distal end 314 of outer sleeve 310.

Inner shaft 350 is axially displaceable relative to outer sleeve 310. Proximal end 352 of inner shaft 350 includes an external thread 353 that engages the internal thread 315 inside knob portion 313. In this arrangement, inner shaft 350 is axially displaceable relative to outer sleeve in response to rotation of knob portion 313. Inner shaft 350 can be advanced through outer sleeve 310 in the distal direction by rotating knob 313 in a first direction. Conversely, inner shaft 350 can be drawn into the outer sleeve 310 in a proximal direction by rotation of knob portion 313 in a second direction opposite the first direction. A handle portion 301 is fixed to proximal end 312 of outer sleeve 310 and acts as a means for holding the outer sleeve in a fixed orientation while knob portion 313 is rotated.

A slide actuator 370 extends along the outer sleeve 310. Slide actuator 370 has a proximal end 372 with a flange 373 and a distal end 374. A guide member mount 380 is pivotally coupled to slide actuator 370. Guide member mount 380 includes a socket 382 configured to hold the end of an elongated guide member 700, as shown in FIG. 1. Guide member mount 380 is slidably mounted to outer sleeve 310 by a pair of pins 384. Pins 384 extend in longitudinal slots 318 formed along outer sleeve 310. Slide actuator 370 is axially displaceable over outer sleeve 310. Longitudinal slots 318 limit the extent to which guide member mount 380 can translate along outer sleeve 310 when slide actuator 370 is displaced over the outer sleeve. Slide actuator 370 is operable to change the orientation of a fixation rod mounted in rod clamp 360. In addition, slide actuator 370 is configured to control the relative orientations of rod clamp 360 and guide member mount 380, and maintain them in a synchronized arrangement that keeps the fixation rod 600 and guide member 700 in identical or nearly identical orientations when moved to raised positions, as described in more detail below.

Instrument 300 is operable by manipulating knob portion 313 and slide actuator 370. To begin, the user inserts an end of fixation rod 600 into rod clamp 360. Knob portion 313 is rotated in a first direction relative to handle portion 301. As knob portion 313 is rotated, outer sleeve 310 advances in a distal direction relative to the inner shaft until the distal end of the outer sleeve slides over the tapered section 361. As the distal end of outer sleeve 310 slides over tapered section 361, the outer sleeve compresses jaws 359 together, which in turn compresses the semi-cylindrical sections 364 of rod clamp 360, securing the rod in the rod clamp.

A guide member 700 is inserted into guide member mount 380. Guide member mount 380 includes a C-shaped body 385 surrounding socket 382. The dimensions of socket 382 are slightly less than the dimensions of guide member 700. Body 385 is partially open on one side and resiliently flexible to allow the body to flex open and expand socket 382, so the socket is wide enough to receive a guide member 700 and hold it with a friction fit.

Figure 18:
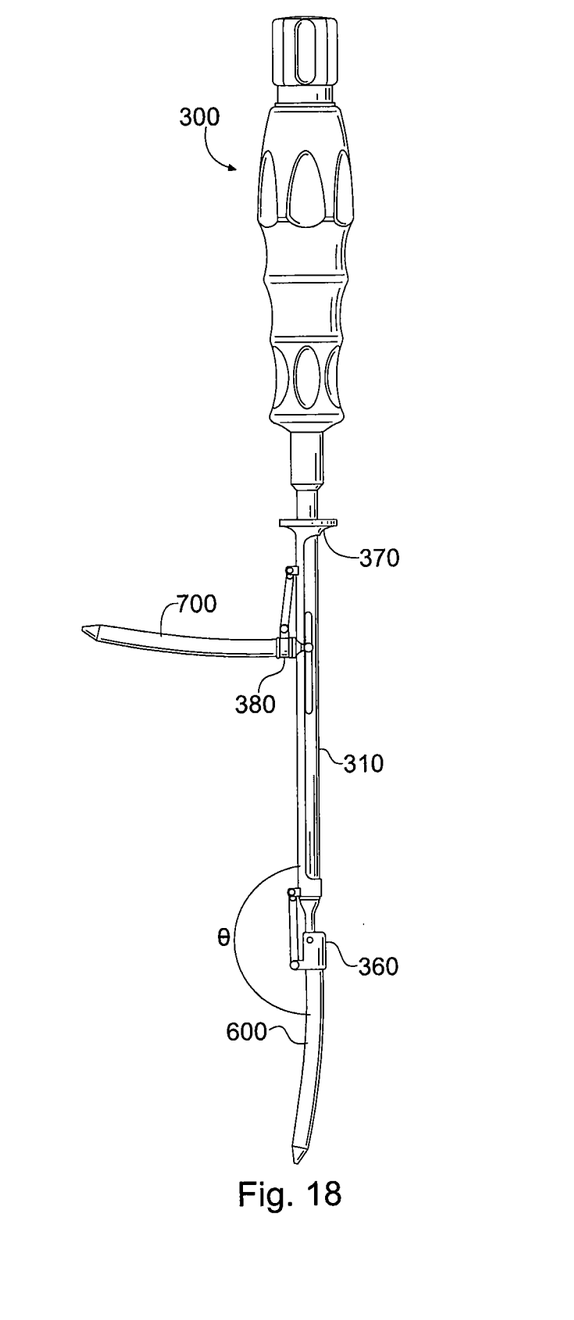
FIG. 18 is a side view of the rod insertion instrument, spinal fixation rod and guide member of FIG. 15, the instrument shown with the rod in a second position.

Slide actuator 370 is moveable along outer sleeve 310 to adjust the orientation of a rod 600 mounted in rod clamp 360. More specifically, slide actuator 370 is movable between a first position, shown in FIG. 15, and a second position, which is shown in FIG. 18. Guide member mount 380 and rod clamp 360 are connected to slide actuator 370 by linkages 375. Linkages 375 indirectly connect guide member mount 380 and rod clamp 360 to one another. In this arrangement, guide member mount 380 is configured to mimic the position of rod clamp 360 as the rod clamp is moved to the first position, as shown in FIG. 15.

In the first position, slide actuator 370 is located in a relatively proximal position on outer sleeve 310 and positions rod 600 in a raised position. In the raised position, the angle $\Theta$ between rod 600 and outer sleeve 310 is approximately 90 degrees. In the second position, slide actuator 370 is located in a relatively distal position on outer sleeve 310 and positions rod 600 in a lowered position. In the lowered position, the angle $\Theta$ between rod 600 and outer sleeve 310 is approximately 180 degrees. During a procedure, slide actuator 370 is moved to the second position to position rod 600 in the lowered position, allowing the rod to be inserted through a small incision or portal. Once rod 600 is inserted into an incision, slide actuator 370 is gradually moved to the first position to move the rod to the raised position, in which the rod can be navigated beneath tissue into the rod receiving implants.

Figure 19:
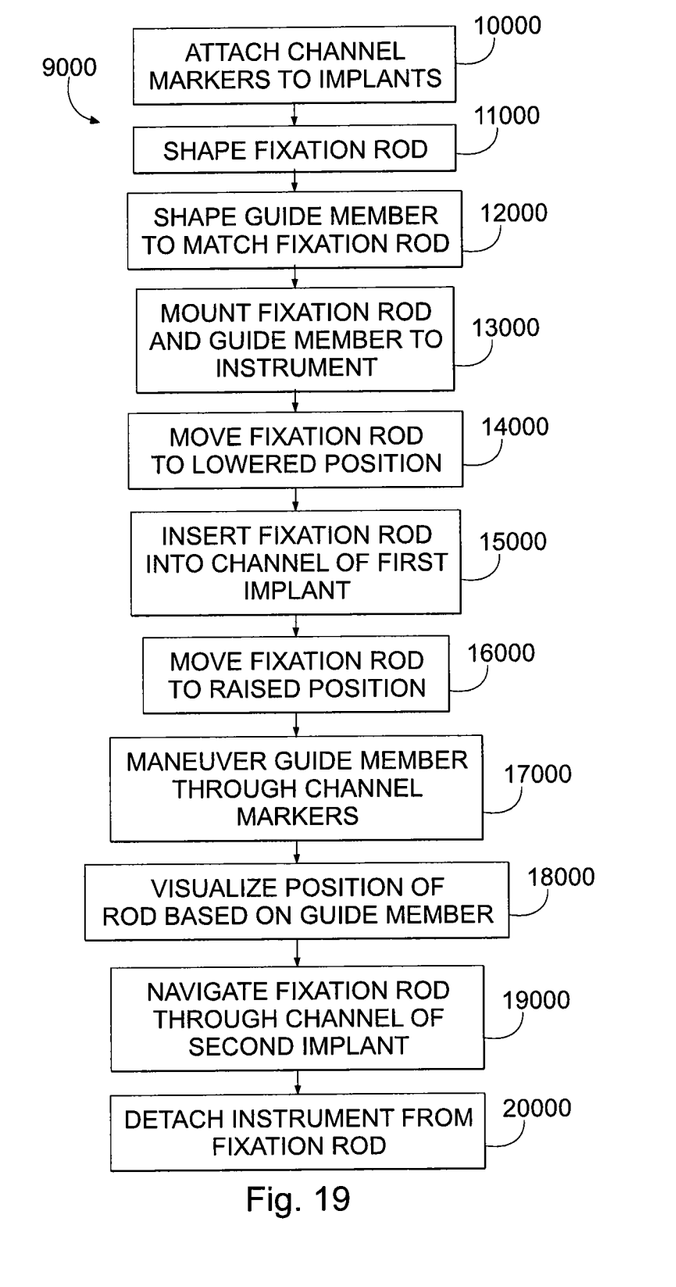
FIG. 19 is a block diagram illustrating steps for inserting a fixation rod in accordance with an exemplary method of the present invention.

Referring now to FIG. 19, a method 9000 for inserting a fixation rod using a rod guidance instrument and rod guidance assembly is illustrated. The method steps in FIG. 19 may be practiced with rod guidance instrument 300 and rod guidance assembly 200. Therefore, the following description uses the names of components that are described in connection with rod guidance instrument 300 and rod guidance assembly 200. It will be understood, however, that rod guidance instrument 300 and rod guidance assembly 200 are exemplary embodiments only, and that the following method may be practiced using variants of those embodiments having analogous components, without departing from the invention. Consequently, the components described in the following method may be associated with rod guidance instrument 300 and rod guidance assembly 200, or variants of those embodiments.

To begin, channel markers are attached to a series of pedicle screw implants in step 10000. As noted above, the channel markers may be attached to extension tubes that are pre-assembled with the pedicle screw assemblies prior to implantation. The channel markers represent the relative positions of the rod receiving channels on the implants, and define the shape to which a fixation rod must conform. In step 11000, a fixation rod is shaped to conform to the path defined by the channel markers. Once the fixation rod is shaped, a guide member or dummy rod is selected and shaped to match the shape of the fixation rod in step 12000. The fixation rod and guide member are then mounted to a rod guidance instrument in step 13000.

The rod guidance instrument is adjusted to move the mounted fixation rod to the lowered position in step 14000. An example of a rod in the lowered position is shown in FIG. 18. The lowered rod in then insertion through an incision and into the rod receiving channel of a first implant in step 15000. The rod guidance instrument is then adjusted to move the fixation rod to a raised position in step 16000. An example of a rod in a raised position is shown in FIG. 15. The guide member moves in unison with the fixation rod to assume a raised position as well, as shown by the example in FIG. 15. The guide member is then maneuvered through the channel markers in step 17000. As this is done, the surgeon visualizes the position of the fixation rod relative to the first implant and a second implant in step 18000. The surgeon visualizes the position and motion of the fixation rod based on the corresponding position and motion of the guide member relative to the channel markers. With this guidance, the surgeon navigates the fixation rod through the rod receiving channel of a second implant in step 19000. In the case of three or more implants, the surgeon continues to navigate the rod by observing the position and movement of the guide member relative to the channel markers. Once the rod is positioned in the channels of all the implants, the instrument is detached from the fixation rod by unlocking the rod clamp to release the rod in step 20000.

While preferred embodiments of the invention have been shown and described herein, it will be understood that the described embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed:

1. A kit for guiding the insertion of a spinal fixation rod, the kit comprising:
    a plurality of hollow elongated extension tubes, each extension tube having an implant engaging end, a template end, and an engagement surface on an outside of the extension tube, the engagement surface having a contour;
    a first tube connector and a second tube connector, wherein the first and second tube connectors are joinable in series, each tube connector comprising a ring surrounding a central opening, the central opening bounded by an inner wall having a contour that conforms to the contour of the engagement surface of one of the extension tubes, wherein the first tube connector further comprises a connector sleeve extending outwardly away from the ring of the first tube connector and the second tube connector further comprises a connector arm extending outwardly away from the ring of the second tube connector, wherein the connector arm is pivotable relative to the ring of the second tube connector; and
    a plurality of rod templates, each rod template comprising a rod receiving channel,
    wherein the connector arm of the second tube connector is inserted in and encompassed by the connector sleeve of the first tube connector.

2. The kit of claim 1, wherein each of the rod templates is detachably connectable to one of the extension tubes.

3. The kit of claim 2, wherein each of the extension tubes comprises a longitudinal axis and a pair of slots extending parallel to the longitudinal axis, the slots opposing one another on opposite sides of the longitudinal axis.

4. The kit of claim 3, wherein each rod template further comprises a stem portion removably inserted into a corresponding one of the slots.

5. The kit of claim 1, further comprising a rod guidance instrument, the rod guidance instrument comprising:
    a sleeve having a handle end and a spinal rod engagement end opposite the handle end, the sleeve comprising a midsection between the spinal rod engagement end and the handle end;
    an elongated guide member pivotally attached to the midsection of the sleeve, the guide member receivable through the rod receiving channels of the rod templates and deformable to a specific curvature.

6. The kit of claim 5 further comprising a spinal fixation rod attached to the spinal rod engagement end of the rod guidance instrument, the guide member and spinal fixation rod having the same length and curvature so as to define parallel spline curves extending from the sleeve.

7. The kit of claim 6, wherein the guide member and spinal fixation rod are interconnected by a linkage, and are movable in unison.

8. The kit of claim 1, wherein each rod template further comprises a ring attachment placed over the template end of each extension tube, the ring attachment having a pair of body portions, each body portion having a U-shaped channel which cooperatively define the rod receiving channel.

9. The kit of claim 1, wherein the engagement surface of each extension tube includes a pair of engagement projections, each rod template further comprises a ring attachment placed over the template end of each extension tube and having a pair of engagement surfaces defined on an inner surface of the ring attachment, the engagement projections of each extension tube engage the engagement surfaces of the ring attachment and prevent the ring attachment from rotating relative to the extension tube.

10. The kit of claim 9, wherein the engagement surfaces are offset from the rod receiving channel.

11. The kit of claim 1, wherein the rod receiving channel is integrally formed in the template end of each extension tube.

12. The kit of claim 1, wherein the second tube connector further comprises an aperture defined therein, the aperture forming a sliding track within the ring of the second tube connector, an end of the connector arm being inserted into the aperture and slidable along the sliding track.

13. The kit of claim 1, wherein an aperture is defined in the connector sleeve and a plurality of slits are formed on the connector arm, at least one slit being visible through the aperture.

14. The kit of claim 13, wherein the connector sleeve further comprises a latch pivotally mounted thereto, the latch being pivotable between a locked position in which a pawl extending from the latch engages the a slit on the connector arm via the aperture defined in the connector sleeve, and a release position in which the pawl is disengaged from the slit.

15. The kit of claim 1, wherein the connector sleeve of the first tube connector is a tubular sleeve.

16. The kit of claim 1, wherein the second tube connector further comprises a connector sleeve extending outwardly away from the ring of the second tube connector.

17. A kit for guiding the insertion of a spinal fixation rod, the kit comprising:
   a rod guidance instrument comprising:
      a sleeve having a handle end and a rod engagement end opposite the handle end, the sleeve comprising a midsection between the handle end and the spinal rod engagement end; and
      an elongated guide member attached to the midsection of the sleeve; and a spinal fixation rod pivotally mounted to the rod engagement end of the sleeve,
   wherein the rod guidance instrument comprises a slide actuator that is axially displaceable over the sleeve between a first position, which pivots the spinal fixation rod to a raised position, and a second position, which pivots the spinal fixation rod to a lowered position;
   a plurality of extension tubes; and
   a first tube connector and a second tube connector, wherein each tube connector includes a ring surrounding a corresponding extension tube, and wherein the first tube connector further comprises a connector sleeve extending away from the ring of the first tube connector and the second tube connector further comprises a connector arm extending away from the ring of the second tube connector, wherein the connector arm of the second tube connector is inserted in and encompassed by the connector sleeve of the first tube connector, and wherein the connector arm is pivotable relative to the ring of the second tube connector.

18. The kit of claim 17, wherein the guide member and spinal fixation rod have the same length and curvature, defining parallel spline curves extending from the sleeve.

19. The kit of claim 17, wherein the guide member and the spinal fixation rod are interconnected by a linkage, and are movable in unison.

20. The kit of claim 17, wherein each extension tube has an implant engaging end, a template end, and an engagement surface on the outside of the extension tube, the engagement surface having a contour.

21. The kit of claim 20, wherein the first and second tube connectors are joinable in series, the ring of each tube connector surrounding a central opening, and the central opening bounded by an inner wall inside the ring, the inner wall having a contour that conforms to the contour of the engagement surface of one of the extension tubes.

22. The kit of claim 20 further comprising a plurality of rod templates, each rod template comprising a rod receiving channel and a mounting end, the mounting end being mountable on the template end of one of the extension tubes.

23. The kit of claim 17, wherein the connector sleeve of the first tube connector is a tubular sleeve.

24. The kit of claim 17, wherein the second tube connector further comprises a connector sleeve extending outwardly away from the ring of the second tube connector.

* * * * *